United States Patent
Albert

(10) Patent No.: US 8,221,727 B2
(45) Date of Patent: Jul. 17, 2012

(54) BEVERAGE FOR ANIMAL DENTAL CARE

(75) Inventor: Karen Albert, Malibu, CA (US)

(73) Assignee: HealthyMouth, LLC, Malibu, CA (US)

(*) Notice: Subject to any disclaimer, the term of this patent is extended or adjusted under 35 U.S.C. 154(b) by 8 days.

(21) Appl. No.: 12/218,106

(22) Filed: Jul. 11, 2008

(65) Prior Publication Data

US 2009/0022673 A1 Jan. 22, 2009

Related U.S. Application Data

(60) Provisional application No. 60/959,101, filed on Jul. 11, 2007.

(51) Int. Cl.
*A61K 7/28* (2006.01)

(52) U.S. Cl. .............. 424/50; 424/58; 424/442

(58) Field of Classification Search ............. 424/49, 424/50, 442, 58
See application file for complete search history.

(56) References Cited

U.S. PATENT DOCUMENTS

| | | | |
|---|---|---|---|
| 6,485,711 B1* | 11/2002 | Olmstead | 424/58 |
| 2003/0064104 A1* | 4/2003 | Stillman | 424/490 |
| 2004/0120991 A1* | 6/2004 | Gardner et al. | 424/443 |
| 2005/0210615 A1 | 9/2005 | Shastry et al. | |
| 2006/0140883 A1* | 6/2006 | Trivedi et al. | 424/58 |
| 2006/0286044 A1* | 12/2006 | Robinson et al. | 424/49 |
| 2007/0009576 A1* | 1/2007 | Stillman | 424/439 |
| 2007/0154558 A1 | 7/2007 | Gaserod et al. | |
| 2007/0253919 A1* | 11/2007 | Boyd | 424/54 |
| 2008/0199412 A1* | 8/2008 | Milanovich et al. | 424/49 |
| 2009/0257962 A1* | 10/2009 | Albert | 424/50 |
| 2009/0280070 A1* | 11/2009 | Porsgaard et al. | 424/48 |

* cited by examiner

*Primary Examiner* — Ralph Gitomer
(74) *Attorney, Agent, or Firm* — Morris O'Bryant Compagni

(57) ABSTRACT

A comestible, water-based composition containing natural ingredients provides an effective amount of at least one active ingredient selected to reduce the proliferation of bacteria in the mouth of animals to treat and improve the dental health of animals. The composition can be administered to animals in the form of their daily intake of water and may be especially packaged for ready use and consumption by animals in prepackaged and portable doses. Compositions containing natural ingredients and formulated as toothpastes for animal dental care are also provided.

5 Claims, No Drawings

US 8,221,727 B2

BEVERAGE FOR ANIMAL DENTAL CARE

CROSS-REFERENCE TO RELATED APPLICATION

This application is a non-provisional application claiming priority to provisional patent application Ser. No. 60/959,101 filed Jul. 11, 2007.

BACKGROUND OF THE INVENTION

1. Field of the Invention

This invention relates to pet care products, and specifically relates to compositions for the benefit of dental care of animals, and a packaging method therefor.

2. Description of Related Art

There has been an increased awareness over the last few decades concerning the criticality of dental health care in the overall well-being of pets, especially dogs and cats. Both dogs and cats are born with deciduous teeth, or baby teeth, that eventually fall out and are replaced by permanent teeth. A dog typically has forty-two permanent teeth and a cat typically has thirty permanent teeth.

The permanent teeth of dogs and cats deteriorate over time and are subject to dental disease similar to human teeth. Amounts of tartar can build up on the permanent teeth and the teeth may become broken or split. Dogs and cats are also susceptible to gum disease and abscesses which become painful for the animal. Gum disease, painful teeth and other dental disease conditions can lead to significant discomfort, loss of appetite and general lethargy in an animal.

Severe dental disease in an animal can adversely affect the heart, kidneys and intestinal tract of the animal, and can spread bacteria to other parts of the body, thereby weakening the health of the animal and decreasing its longevity.

The veterinary industry has recognized these dental problems for some time and recommends that pets be provided with regular dental care as part of the regular health maintenance of pets. It is recommended that dental care be started when animals are small, in the puppy or kitten stage, and that regular dental procedures be followed by both the pet owner and the veterinarian. Such dental procedures include the owner brushing the teeth of the pet using toothbrushes and toothpaste especially formulated for dogs and cats, and getting regular dental check-ups from the veterinarian.

Many pet owners aid in the dental care of their pets by brushing the animal's teeth on a recommended schedule. However, most animals find the process unpleasant and it may become difficult to hold an animal in place while the toothbrushing procedure takes place. Taking the animal to the veterinarian, while recommended, may not be possible or practicable on a regular and repeated basis and the tooth cleaning process is very costly.

Therefore, it would be beneficial to pet owners to provide means for maintaining the dental healthcare of pets, especially dogs and cats, as an overall program of dental care for the animal, and to provide such means in an easily administered and natural form, for both the sake of the pet and the pet owner.

BRIEF SUMMARY OF THE INVENTION

In accordance with the present invention, comestible, non-medicated compositions are provided for treating and improving the dental health of animals. The compositions are water-based products that can be administered to pets by their owners as a cost effective and easily administered means of caring for the dental health of pets. As part of the invention, the compositions may be especially packaged for ready use and consumption by animals in pre-packaged and portable doses.

In one embodiment of the invention, a composition is provided in a water-based form that is administered to the animal as the animal's daily intake of water. The formula contains natural ingredients which aid in reduction of bacteria in the mouth, thereby reducing plaque and the production of tartar. The composition contains natural ingredients that freshen the breath of the animal and act like a mouthwash that helps prevent the accumulation of bacteria. The formulation also acts to coat the buccal cavity of the animal to provide continuous protection against the accumulation of bacteria.

The water-based composition of the invention is predominantly water, and can thereby satisfy the fluid consumption needs of the animal while also providing a dental health care treatment. The composition includes natural ingredients that provide various benefits toward reducing bacteria and freshening the animal's breath.

In another embodiment of the invention, a dentifrice in the form of a toothpaste is provided which contains natural ingredients that aid in the reduction of bacteria and plaque. The toothpaste composition is formulated for use in brushing the teeth of the animal in a conventional manner.

While the embodiments of the invention are described herein with respect to dogs and cats, the compositions and formulations of the invention are not limited to use in dogs and cats. The formulas and compositions can be used and/or adapted for use with any water-consuming animal regardless of whether such animal is maintained as a pet.

DETAILED DESCRIPTION OF THE INVENTION

In a first embodiment of the invention, a comestible water product is formulated to provided an animal with its daily consumption of water while providing, in that water, natural ingredients that aid in the reduction of bacteria in the mouth and freshen the animal's breath. The composition includes at least two active ingredients which mediate the reduction of bacteria in the animal's mouth.

An example of one active ingredient that may be used in the composition is one or more natural enzymes, such as papain, bromelain or other similar enzyme, or combinations thereof. Such enzymes may be included in the composition to effectively reduce the build up of proteins in the mouth and thereby reduce bacterial proliferation.

Other active ingredients may include one or more antibacterial agents that effectively reduce bacterial proliferation. Many such antibacterial agents are known and may be used in the composition. One particularly beneficial example of an antibacterial agent is zinc gluconate.

The composition may also include natural antioxidants that increase the pet's immune response to bacteria. Such antioxidants may include, for example, grape skin extract, grape seed extract, blueberry extracts, pomegranate extract, beet extract and other anthocyanins or similar antioxidants derived from edible and natural sources. These antioxidants derived from natural sources may be in a freeze-dried and powdered form, although other forms may be suitable for use in the composition.

The composition may also include vitamins which are also antioxidants and which help increase the immune response to bacteria. For example, the composition may include vitamins B and C, as well as other vitamins. It has been shown that the antioxidant effects of anthocyanins and vitamins have a greater effect in combination than such antioxidants alone, thereby providing a beneficial cumulative effect.

The composition may include chlorophyll as a natural substance for freshening the animal's breath. Flavoring agents may be added as well to not only improve the palatability of the composition, but to enhance the ability of the composition to produce fresher breath in the animal. Flavoring agents may include, by way of example only, extracts of clove and cinnamon. Any number of other flavoring agents may be used, as well.

The composition may also include agents that help coat the animal's mouth with the fluid of the composition to increase its overall effectiveness. Such agents may include glycerin, which itself has antiseptic properties, sorbitol and zinc gluconate. Certain gums, such as xanthan gum, also provide increased adherence of the formula to the teeth and gums. By formulating the composition with agents that provide or increase the adherence of the composition to the animals teeth, gums and mouth, the effective ingredients are able to act longer to kill bacteria or resist bacterial buildup. The animal's breath will stay fresher for a longer time as well.

An exemplar formulation of the composition is as follows:

| Purified Water | 70% to 90% by weight |
| --- | --- |
| Glycerin | 5.0% to 10.0% by weight |
| Grape Skin Extract◆ | 0.1% to 1.0% by weight |
| Yucca Extract | 0.1% to 1.0% by weight |
| Zinc Gluconate | 0.01% to 0.2% by weight |
| Grape Seed Extract◆◆ | 0.01% to 0.2% by weight |
| Papain | 0.01% to 0.2% by weight |
| Riboflavin | 0.01% to 0.08% by weight |
| Ascorbic acid | 0.01% to 0.1% by weight |
| Clove Extract | 0.01% to 0.1% by weight |
| Cinnamon Extract | 0.01% to 0.1% by weight |
| Chlorophyll | 0.01% to 0.5% by weight |
| Sorbic Acid | 0.01% to 0.1% by weight |

◆Pomegranate may be substituted for Grape Skin Extract in equal amount
◆◆Blueberry can be substituted for Grape Seed Extract in equal amount The composition is made by adding the glycerin to approximately three-quarters of the amount of purified water in a stainless steel tank equipped with a mixing apparatus. The mixture is stirred until well-blended. The grape skin extract, Yucca extract, riboflavin, ascorbic acid, sorbic acid, zinc gluconate, papain, grape seed extract, clove extract and cinnamon extract are then added and the mixture is stirred until a homogeneous fluid is achieved. The chlorophyll is then added and the material is stirred until the chlorophyll is uniformly mixed throughout. The balance of purified water is added and mixed until uniformly distributed.

The foregoing mixture provides a concentrate from which is prepared the final product dosage. To one quart, or approximately 1000 ml, of purified water is added five milliliters (5 ml) of the concentrate. The resulting quantity of the composition is then placed in appropriate containers containing a desired amount of the composition.

A single daily dose of the composition for both cats and dogs is from between about 100 ml to about 2000 ml, with a recommended minimum effective daily dose of about 200 ml. Animals will tend to drink the amount of water that is needed to stay hydrated, and an animal can, therefore, consume whatever amount of the composition is required for the animal's hydration needs. The composition is not toxic and it is virtually impossible to consume too much of the composition in a day.

A daily dosage, or any desired amount, of the composition can be packaged in any appropriate container, such as a bottle, that can be opened and poured into the pet's bowl. A single recommended dosage of 200 ml, or several dosages, can be contained in, for example, a bottle with instructions for metering out the appropriate amount of fluid to the animal in a given day.

In a particularly suitable packaging arrangement, a desired amount of the composition can be contained in a closed, resealable container sized for feeding the animal. An exemplary container is disclosed in co-pending U.S. application Ser. No. 12/154,850 which describes a container that can be sized and shaped in the form of a feeding bowl for the pet. The container is resealable, portable, reusable and recyclable. The container can be filled with the appropriate amount of a single or daily dosage of the composition to facilitate administration of the appropriate amount of fluid to the animal in a given day.

In two studies conducted using forty dogs in each study, the dogs were divided into a first test group of twenty animals who received the formulated water composition of the present invention and a second test group of twenty animals who received plain water. Prior to the study, all of the animals received teeth cleaning by a professional veterinarian or professional dental hygienist. All dogs were scored at a plaque level of zero following the cleaning.

The composition of the present invention was added to filtered water for the first test group (i.e., the treated animals) and filtered tap or plain water was administered to the second test group as a control. Each of the forty animals in the two studies were examined and scored for plaque every seven days during a twenty-eight day study period. Health examinations were conducted on each of the animals with laboratory profiles being generated for CBC, chemistry profile, thyroid profile, vaccine titers, von Willebrand factor activity, infectious disease screening, urinalysis and fecal ova and parasite screening. All animals were fed twice a day with the same food in an amount consistent with the animal's body size and weight.

Plaque scoring was conducted on each animal, testing the individual teeth of the upper jaw and the individual teeth of the lower jaw, and plaque index and points were assigned as follows:

| 0 = no plaque | 1 < ⅓ with plaque |
| --- | --- |
| 2 = ⅓ to ⅔ with plaque | 3 > ⅔ with plaque |

The data derived from the first study are as follows:

| STUDY 1 | | |
| --- | --- | --- |
| | Upper Jaw-Plaque Points | % Plaque Remaining |
| Test Subjects (20) | 153 | 20% |
| Control Subjects (20) | 610 | 80% |
| Total Points (40) | 763 | 100% |
| | Lower Jaw-Plaque Points | % Plaque Remaining |
| Test Subjects (20) | 144 | 23% |
| Control Subjects (20) | 486 | 77% |
| Total Points (40) | 630 | 100% |

The test data derived from the second study are as follows:

| STUDY 2 | | |
| --- | --- | --- |
| | Upper Jaw-Plaque Points | % Plaque Remaining |
| Test Subjects (20) | 79 | 18.5% |
| Control Subjects (20) | 349 | 81.5% |
| Total Points (40) | 428 | 100% |
| | Lower Jaw-Plaque Points | % Plaque Remaining |
| Test Subjects (20) | 73 | 19.4% |
| Control Subjects (20) | 304 | 80.6% |
| Total Points (40) | 377 | 100% |

In each study, a softening of plaque was noticed in the treated group (i.e., the group that was administered the composition of the present invention) soon after the trials began, and the plaque could be easily wiped away with a gauze pad. A significant reduction in plaque occurrence in the treated group was observed in both of the studies, as demonstrated in the summarized data, above. The scoring in the upper and lower jaws, in both studies, averaged an 80% scoring in remaining plaque while there was a 20% scoring of remaining plaque in the untreated group. The results demonstrate that administering the composition of the present invention to animals on a daily basis should significantly reduce the buildup of plaque and heavy tartar, thereby improving the overall dental health of the animal.

In another embodiment of the present invention, toothpaste compositions are made of natural ingredients and are formulated for use in brushing an animal's teeth. The natural ingredients in the toothpaste formula are selected to provide cleaning, antibacterial protection and/or breath freshening benefits. An exemplar formula for a toothpaste that may be used for dogs is as follows:

| | |
| --- | --- |
| Purified water | 10.0% to 20.0% by weight |
| Sorbitol | 15.0% to 30.0% by weight |
| Sodium bicarbonate† | 25.0% to 45.0% by weight |
| Glycerin | 10.0% to 20.0% by weight |
| Potassium Sorbate | 0.01% to 0.5% by weight |
| Flavor | 0.10% to 0.5% by weight |
| Tetrasodium Pyrophosphate | 1.0% to 6.05% by weight |
| Chlorophyll | 0.01% to 0.1% by weight |
| Xanthan gum | 0.05% to 2.0% by weight |

†Calcium carbonate may be substituted in equal amount

The toothpaste composition for dogs noted above may also be formulated with other beneficial additives, such as blueberry, pomegranate, cinnamon, clove and zinc gluconate, their beneficial properties having been noted previously.

The toothpaste composition is made by adding the purified water to a clean stainless steel vessel and heating the water to 50° C. The potassium sorbate is then added and mixed until dissolved. The sorbitol, flavor and chlorophyll are added to the water one ingredient at a time and the fluid is mixed thoroughly to dissolve or disperse the ingredient into solution. The bicarbonate, or carbonate, is added to the fluid in the vessel and stirred constantly to keep it in solution. The tetrasodium pyrophosphate is then added and kept in suspension with constant stirring of the mixture. In a separate vessel, the xanthan gum is dispersed in the glycerin and is mixed until the gum is evenly dispersed. The gum and glycerin mixture is then added to the fluid in the main vessel and mixed until all ingredients are evenly dispersed and the mixture is thick. The mixture is then packaged in appropriate containers.

An exemplary formula for a toothpaste that may used with cats is as follows:

| | |
| --- | --- |
| Purified water | 10% to 20% by weight |
| Sorbitol | 20% to 30% by weight |
| Sodium bicarbonate† | 30% to 45% by weight |
| Glycerin | 10% to 20% by weight |
| Potassium Sorbate | 0.1% to 0.5% by weight |
| Natural Fish Flavor | 0.1% to 0.5% by weight |
| Tetrasodium Pyrophosphate | 2% to 6% by weight |
| Chlorophyll | 0.01% to 0.1% by weight |
| Xanthan gum | 0.1% to 0.5% by weight |
| Fish Oil | 0.05% to 0.3% by weight |
| Taurine | 0.01% to 0.1% by weight |
| Cinnamon extract | 0.01% to 0.5% by weight |
| Clove Extract | 0.01% to 0.5% by weight |
| Pomegranate | 0.1% to 1.0% by weight |
| Blueberry Extract | 0.05% to 0.5% by weight |
| Zinc Gluconate | 0.05% to 0.5% by weight |
| Papain | 0.05% to 0.5% by weight |

†Calcium carbonate may be substituted in equal amount

The toothpaste formulation for cats is made by placing the purified water in a clean stainless steel vessel and heating the water to 50° C. The potassium sorbate is then added and mix until dissolved. The zinc gluconate is next added and mixed until dissolved into solution. The sorbitol is added and mixed, followed by addition of the papain, cinnamon and cloves, and the mixture is stirred until all ingredients are evenly dispersed. The pomegranate, blueberry and chlorophyll are then added and the mixture stirred until all ingredients are evenly dispersed. The bicarbonate or carbonate is then added and the solution is mixed to keep the bicarbonate or carbonate in suspension. The tetrasodium pyrophosphate is then added and the solution mixed to maintain the ingredients in suspension. In a separate vessel, the xanthan gum is added to the glycerin and mixed until the gum is evenly dispersed. The gum and glycerin mixture is then added to the solution in the main vessel and the mixture is mixed until all ingredients are evenly dispersed and the mixtures is thickened. The resulting composition is then packaged in an appropriate container.

The water and toothpaste compositions of the present invention are directed to improving the dental health of animals by providing natural ingredients that reduce plaque buildup and tartar, and to freshening the breath of the animal. The formulas and compositions disclosed herein are by way of example and can be adapted for use with any animal that drinks water. Thus, reference herein to specific details of the formulas and compositions is by way of example and not meant to limit the scope of the invention.

What is claimed is:
1. A liquid concentrate suitable for dilution to form a non-toxic beverage for non-human animals to consume in amounts sufficient to provide the daily hydration requirements of the animal, comprising:
about 70% to about 90% by weight water;
about 5% to about 10% by weight of at least one adhering agent suitable for causing fluid to adhere to the mouth of an animal for a time sufficient to effect reduction of bacteria in the animal's mouth;
about 0.1% to about 2.0% by weight of at least one active ingredient suitable for reducing bacteria in the mouth of a non-human animal, said at least one active ingredient being selected from the group consisting of enzymes in combination with extract of cinnamon and extract of clove;

about 0.1% to about 1.0% of Yucca extract;

about 0.01% to about 2.5% by weight of an antioxidant agent.

2. The liquid concentrate according to claim 1 wherein said enzyme is papain.

3. The liquid concentrate according to claim 1 wherein said adhering agent is selected from the group comprising glycerine, sorbitol, zinc gluconate and combinations thereof.

4. The liquid concentrate according to claim 1 wherein said at least one antioxidant agent is derived from an edible and non-toxic natural source and is selected from the group comprising grape skin extract, grape seed extract, blueberry extract, pomegranate extract, beet extract, anthocyanins and combinations thereof.

5. A liquid concentrate suitable for dilution to form a non-toxic beverage for non-human animals to consume in amounts sufficient to provide the daily hydration requirements of the animal, consisting essentially of:

about 70% to about 90% by weight water;

about 5% to about 10% by weight of at least one adhering agent suitable for causing fluid to adhere to the mouth of an animal for a time sufficient to effect reduction of bacteria in the animal's mouth, said at least one adhering agent being glycerin or zinc gluconate, or combinations thereof;

about 0.1% to about 2.0% by weight of an active ingredient, comprising an enzyme selected from the group comprising papain and bromelain, in combination with extract of cinnamon and extract of clove;

about 0.1% to about 1.0% of Yucca extract as a surfactant;

at least one antioxidant agent in an amount of from between about 0.01% to about 2.5% by weight, said at least one antioxidant agent being derived from an edible and non-toxic natural source and being selected from the group consisting of grape skin extract, grape seed extract, blueberry extract, pomegranate extract, beet extract, anthocyanins and combinations thereof;

at least one vitamin in an amount of from between about 0.01% to about 0.2% by weight selected from the group consisting of vitamin B and vitamin C; and at least one non-toxic flavoring agent in an amount of from between about 0.01% to about 0.2% by weight.

* * * * *